United States Patent
Toyota et al.

(10) Patent No.: US 8,366,639 B2
(45) Date of Patent: Feb. 5, 2013

(54) BALLOON FOR MEASURING PRESSURE RELATED TO ORAL CAVITY AND METHOD FOR PRODUCING THE SAME

(75) Inventors: Koichiro Toyota, Hiroshima (JP); Hideki Munekuni, Tokyo (JP); Hisashi Miyata, Toyama (JP)

(73) Assignee: JMS Co., Ltd., Hiroshima (JP)

( * ) Notice: Subject to any disclaimer, the term of this patent is extended or adjusted under 35 U.S.C. 154(b) by 516 days.

(21) Appl. No.: 12/593,204

(22) PCT Filed: Feb. 8, 2008

(86) PCT No.: PCT/JP2008/052169
§ 371 (c)(1),
(2), (4) Date: Sep. 25, 2009

(87) PCT Pub. No.: WO2008/117574
PCT Pub. Date: Oct. 2, 2008

(65) Prior Publication Data
US 2010/0121224 A1    May 13, 2010

(30) Foreign Application Priority Data
Mar. 26, 2007    (JP) .................................. 2007-079658

(51) Int. Cl.
*A61B 5/117* (2006.01)
*A61B 5/103* (2006.01)
*A61B 5/00* (2006.01)

(52) U.S. Cl. ........................ 600/587; 600/561

(58) Field of Classification Search .................. 600/587, 600/561, 590; 606/108
See application file for complete search history.

(56) References Cited

U.S. PATENT DOCUMENTS

| 5,119,831 | A | 6/1992 | Robin et al. |
| 5,565,165 | A | 10/1996 | Matsuhashi |
| 5,609,161 | A | 3/1997 | Tura et al. |
| 2005/0222584 | A1* | 10/2005 | Kilpatrick et al. ............ 606/108 |
| 2010/0222706 | A1* | 9/2010 | Miyahara et al. ............. 600/590 |

FOREIGN PATENT DOCUMENTS

| EP | 0 730 942 A1 | 9/1996 |
| EP | 1 921 432 A1 | 5/2008 |
| JP | 2001-275994 A | 10/2001 |
| JP | 2003-144553 A | 5/2003 |
| JP | 2005-296281 A | 10/2005 |
| WO | WO 2007/026488 A1 | 3/2007 |

* cited by examiner

*Primary Examiner* — Brian Szmal
(74) *Attorney, Agent, or Firm* — Hamre, Schumann, Mueller & Larson, P.C.

(57) ABSTRACT

A balloon including: a pressure-receiving portion formed of an elastic material and forming an enclosed space; and a tubular portion formed integrally therewith. The balloon is configured to detect the air pressure in the pressure-receiving portion due to communication with a pressure detector through an opening end of the tubular portion. A transverse cross-section of the pressure-receiving portion orthogonal to the axial direction of the tubular portion has a flattened outer circumferential shape with an oblateness f=(A−B)/A, where A represents the length of a major axis of the outer circumferential shape and B represents the length of a minor axis thereof, being set to a range of 0.1≦f≦0.7 at a position at which the length A is at a maximum. The air pressure can be changed significantly and stably, and the precision of the pressure measurement can be increased.

7 Claims, 5 Drawing Sheets

BALLOON FOR MEASURING PRESSURE RELATED TO ORAL CAVITY AND METHOD FOR PRODUCING THE SAME

TECHNICAL FIELD

The present invention relates to a balloon that is used as a pressure receiver to measure a pressure related to the oral cavity, such as the tongue pressure, the pressure of the muscles under the tongue, the lip pressure, the cheek pressure, and the like, for the purpose of diagnosing the functions of the tongue, the muscles under the tongue, the lips, the cheeks, and the like and other purposes.

BACKGROUND ART

In recent years, maintenance and restoration of the ingestion and deglutition functions of elderly people have been pursued, and it is becoming increasingly necessary to elucidate those functions. The movement of the tongue is deeply involved in ingestion and deglutition, and sufficient tongue pressure is needed to form a food bolus and transfer it into the pharynx. Therefore, the measurement and analysis of tongue pressure have important implications. Moreover, measurements of a pressure related to the oral cavity are required for various other purposes.

As an apparatus for measuring a pressure related to the oral cavity, for example, Patent Document 1 discloses an apparatus for measuring the tongue pressure that uses a balloon as a pressure-receiving portion. This apparatus is arranged so that the balloon is inserted into the oral cavity and pressed by the tongue, and the air pressure is detected and converted into an electrical signal at a converting portion communicating with the balloon.

However, handling of the apparatus disclosed in Patent Document 1, such as the attachment and detachment of the balloon portion to and from the transducer, is not necessarily easy, so the apparatus has a problem with practicality. Moreover, since the apparatus employs a structure in which only the balloon is inserted into the oral cavity, in the case where a subject bites the balloon when applying a pressure thereon, a portion in the vicinity of an outlet of the balloon leading to the transducer is pressed down, resulting in a risk that the air pressure will not be transmitted properly to the transducer.

To address these issues, Patent Documents 2 and 3 disclose apparatuses for measuring a pressure related to the oral cavity, the apparatuses being arranged so that a balloon formed of an elastic material is attached to a probe tube and used as a probe, and the probe tube is connected to a pressure detector during use. The interior of the balloon communicates with the pressure detector via the probe tube, and the air pressure inside the balloon can be detected. The use of the probe tube improves the measurement stability as compared with the case where only a balloon is inserted into the oral cavity, facilitates the attachment and detachment of the probe, and increases the ease of handling. Furthermore, a configuration in which the probe tube is connected to a pressurizer as well as the pressure detector and the interior of the balloon is pressurized to a predetermined pressure by a pressurizing portion to increase the precision of the pressure measurement also is disclosed.

Patent Document 1: U.S. Pat. No. 5,609,161
Patent Document 2: JP 2005-296281A
Patent Document 3: JP 2001-275994A

DISCLOSURE OF INVENTION

Problem to be Solved by the Invention

However, with regard to conventional apparatuses for measuring a pressure related to the oral cavity, the form of the balloon is not optimized sufficiently for the measurement of pressure, and there are the following problems.

Conventionally, balloons for measuring a pressure related to the oral cavity are produced by dip molding using a natural rubber. However, in the case where dip molding is employed to shape balloons, variations in quality are likely to occur among the finished products. This results in an error in the value measured using such a balloon. Moreover, it is desirable that a tubular portion of the balloon has a small diameter so that it is easy to close the mouth firmly after the insertion of the balloon into the oral cavity. However, in the case where dip molding is employed to shape balloons, there is a limit to the extent the diameter of the tubular portion can be reduced. Specifically, the reason for this is that in dip molding, if the difference in diameter between the pressure-receiving portion and the tubular portion of a balloon is too great, it is difficult to remove the balloon from the mold. This also leads to a deterioration of the productivity, which results in an increase in cost. Therefore, dip molding is not suitable for the production of balloons for measuring a pressure related to the oral cavity. Moreover, when a natural rubber is used as the raw material for balloons, the natural rubber can cause an allergic reaction in some users, and there also is a problem with safety.

To address these problems, the inventors of the present invention studied various materials and methods for shaping a balloon and concluded that a method that uses a thermoplastic elastomer and applies a blow molding method is suitable for the manufacture of balloons for measuring a pressure related to the oral cavity. It was found that variations in quality among products can be suppressed with this method. Furthermore, an application of a blow molding method eliminates the problem that, as in dip molding, if the difference in diameter between the pressure-receiving portion and the tubular portion of a balloon is too great, it is difficult to remove the balloon from the mold.

However, it was found that balloons for measuring a pressure related to the oral cavity that are formed using a thermoplastic elastomer have the following problems. Specifically, in the case of a balloon having a circular transverse cross-section, the relationship of a load applied to the balloon versus a detected pressure detected using the balloon is not represented by a straight line, but rather by a sigmoid curve. In the case where a balloon having such a property is used to measure pressure, the pressure detection sensitivity varies depending on the range of the load applied to the balloon, so that it is difficult to maintain constant measurement precision over a wide load range.

Moreover, in the case of a balloon having a circular transverse cross-section, it is difficult to hold the balloon stably in position within the oral cavity due to its shape. Thus, it is difficult to change the air pressure in the balloon significantly and stably, and so there also is a problem in that the precision in measuring a pressure applied to the balloon based on changes in the air pressure is not stable.

The present invention has been conceived to address the above-described problems, and it is an object of the invention to provide a balloon for measuring a pressure related to the oral cavity that is capable of changing the air pressure significantly and stably in the oral cavity and providing a favorable linear relationship between the load and the detected pressure, thereby improving the precision of the measurement of a pressure related to the oral cavity.

It also is an object of the invention to provide a method for producing a balloon for measuring a pressure related to the oral cavity, which is capable of suppressing variations in quality and stably manufacturing such a balloon.

Means for Solving Problem

A balloon for measuring a pressure related to the oral cavity of the present invention includes: a pressure-receiving portion that is formed of an elastic material and that internally forms an enclosed space; and a tubular portion that is formed integrally with the pressure-receiving portion, and is configured to detect the air pressure in the interior of the pressure-receiving portion by communicating the interior of the pressure-receiving portion with a pressure detector through an opening end of the tubular portion. A transverse cross-section of the pressure-receiving portion orthogonal to the axial direction of the tubular portion has a flattened outer circumferential shape with an oblateness f=(A−B)/A, where A represents the length of a major axis of the outer circumferential shape and B represents the length of a minor axis thereof being set to a range of $0.1 \leq f \leq 0.7$ at a position at which the length A of the major axis is at a maximum.

In a method for producing a balloon for measuring a pressure related to the oral cavity of the present invention, the balloon includes a pressure-receiving portion that is formed of an elastic material and that internally forms an enclosed space; and a tubular portion that is formed integrally with the pressure-receiving portion, and is configured to detect the air pressure in the interior of the pressure-receiving portion by communicating the interior of the pressure-receiving portion with a pressure detector through an opening end of the tubular portion. The method comprises: setting a transverse cross-section of the pressure-receiving portion orthogonal to the axial direction of the tubular portion to have a flattened outer circumferential shape with an oblateness f=(A−B)/A, where A represents the length of a major axis of the outer circumferential shape and B represents the length of a minor axis thereof, being within a range of $0.1 \leq f \leq 0.7$ at a position at which the length A of the major axis is at a maximum; using a thermoplastic elastomer as a material; and forming the tubular portion and the pressure-receiving portion by blow molding.

Effects of the Invention

According to the configuration of the balloon for measuring a pressure related to the oral cavity of the present invention, even in the case of a balloon that is formed using a thermoplastic elastomer, the linearity of the relationship between the load and the detected pressure can be improved, and the precision of the measurement of a pressure related to the oral cavity can be increased. Moreover, due to its flattened transverse cross-sectional shape, the balloon is more likely to be stably held in position within the oral cavity than in the case of a circular transverse cross-sectional shape, and also when the balloon is compressed with the tongue, the way it is compressed is less likely to vary among individuals.

Furthermore, according to the method for producing a balloon for measuring a pressure related to the oral cavity of the present invention, a balloon having properties as described above can be easily manufactured so as to have a pressure-receiving portion larger than the tubular portion, while suppressing variations in quality, by using a blow molding method.

DESCRIPTION OF REFERENCE NUMERALS

Figure 1:
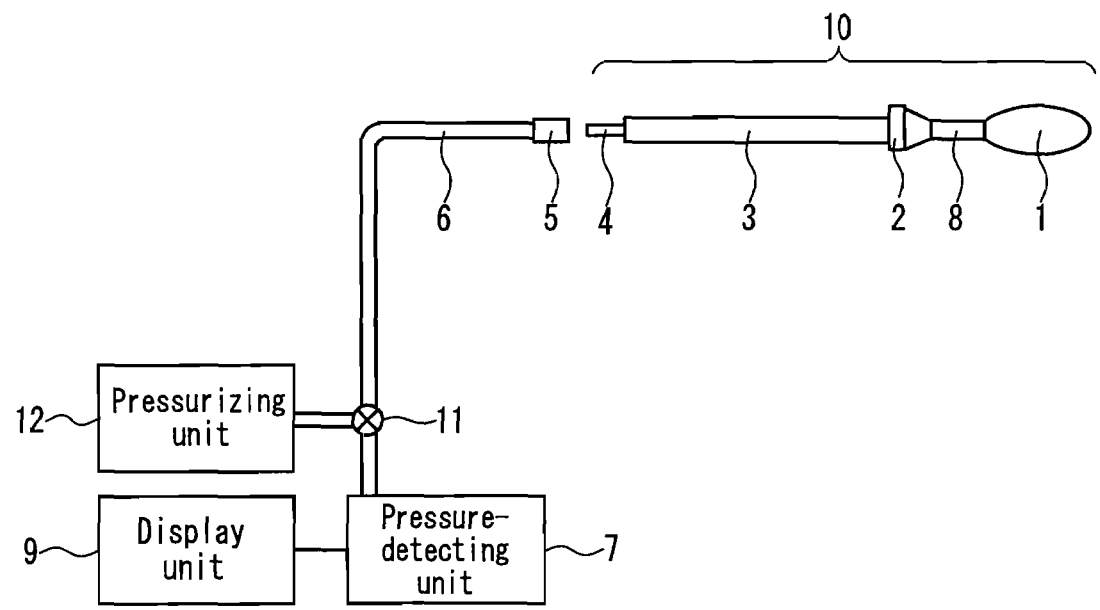
FIG. 1 is a diagram schematically showing the configuration of an apparatus for measuring a pressure related to the oral cavity according to Embodiment 1.

1 Balloon
2 Clamping ring
3 Probe tube
4 Male fitting portion
5 Female fitting portion
6 Apparatus-side tube
7 Pressure-detecting unit
8 Hard ring
9 Display unit
10 Probe
11 Valve
12 Pressurizing unit
13 Teeth
14 Tongue
20 Pressure-receiving portion
21 Tubular portion
22 Flange portion
23, 24 Split mold section
25 Blowing nozzle
26 Blocking portion
P Parting line

DESCRIPTION OF THE INVENTION

The balloon for measuring a pressure related to the oral cavity and the method for producing the same according to the present invention have the above-described configurations as basic configurations, and embodiments as described below are possible.

That is to say, in the balloon for measuring a pressure related to the oral cavity having the above-described configuration, it is preferable that the ratio of the outer diameter of the tubular portion to the length B of the minor axis of the pressure-receiving portion is 5 to 50%. Setting the ratio to not greater than 50% provides a shape that makes it easy to close the mouth firmly after the insertion of the balloon into the oral cavity, and thus is desirable in measuring a pressure related to the oral cavity. Moreover, in the case where the ratio is 5% or less, the tubular portion is too narrow, which results in problems in that it is difficult for air to pass through the tubular portion, the tubular portion is easily damaged, and so on.

Moreover, it is preferable that the balloon for measuring a pressure related to the oral cavity of the present invention is formed of a thermoplastic elastomer. By using a thermoplastic elastomer as the raw material, variations in quality can be suppressed; thus, the quality can be stabilized.

It is preferable that the hardness of the thermoplastic elastomer based on the type A durometer hardness test specified in JIS K 6253 is within a range of A20 to A60. In the case where the hardness is excessively low, the balloon is overinflated or is inflated locally when the internal pressure of the balloon is increased by pressurizing or pressing the balloon, and so an excessively low hardness is not preferable for measurements of a pressure related to the oral cavity. Moreover, in the case where the hardness is excessively high, conversely, the balloon is hard to compress, and the following problems arise: measurements in a low-load region cannot be performed satisfactorily, the relationship between the load applied to the balloon and the detected pressure that is detected according to the load is not constant, and so on. More preferably, the hardness of the thermoplastic elastomer is within a range of A30 to A50.

It should be noted that the hardness as described hereinbelow is a hardness based on the type A durometer hardness test specified in JIS K 6253.

Moreover, it is preferable that the pressure-receiving portion has a wall thickness of 0.1 to 2.0 mm. When the wall thickness of the balloon is thin, the measurement precision of the detected pressure can be increased, but an excessively thin wall thickness results in the formation of a local bulge. Therefore, by setting the wall thickness of the pressure-receiving portion to a range of 0.1 to 2.0, the occurrence of a local bulge can be avoided while improving the measurement precision of the detected pressure. More preferably, the wall thickness is 0.2 to 1.6 mm.

Moreover, it is preferable that the pressure-receiving portion has a length of 15 to 30 mm, and a transverse cross-section of the pressure-receiving portion having the maximum dimensions has an outer circumferential shape in which the length A of the major axis is 15 to 25 ram and the length B of the minor axis is 10 to 20 mm. By setting a size as described above, first, a balloon having a size that makes it easy to install the balloon stably within the oral cavity can be obtained. Moreover, since an easy-to-swallow size of a "food bolus", which is formed by the tongue when a person swallows a substance, is almost the same as the above-described size set for the shape of the balloon, the above-described setting is desirable in measuring the functions of the tongue.

It is possible to configure a probe for measuring a pressure related to the oral cavity, including the balloon for measuring a pressure related to the oral cavity having any one of the above-described configurations; and a cylindrical probe tube is coupled at one end to the tubular portion of the balloon in an airtight manner, wherein a coupling portion that can be coupled removably to the pressure detector is formed at the other end of the probe tube.

Moreover, it is possible to configure an apparatus for measuring a pressure related to the oral cavity, including the balloon for measuring a pressure related to the oral cavity having any one of the above-described configurations; a pressure detector; and a connecting member that provides a connection between the pressure detector and the balloon for measuring a pressure related to the oral cavity to allow the interior of the balloon to communicate with the pressure detector, wherein the air pressure in the interior of the balloon can be detected by the pressure detector.

In the method for producing a balloon for measuring a pressure related to the oral cavity of the present invention having the above-described configuration, it is preferable that the ratio of the outer diameter of the tubular portion to the length B of the minor axis of the pressure-receiving portion is 5 to 50%.

Moreover, it is preferable that the hardness of the thermoplastic elastomer based on the type A durometer hardness test specified in JIS K 6253 is within a range of A20 to A60.

Moreover, it is preferable that a split mold having a parting line that is positioned so as to be in a plane containing the axis of the tubular portion and the major axis of the pressure-receiving portion is used as a metal mold for performing the blow molding. In the case where the parting line is not on the major axis of the pressure-receiving portion, the following problems arise: the shape of the balloon becomes distorted when the balloon is inflated, variations in measurement results occur in the case where a distorted portion is compressed, it is unpleasant to touch, and so on. In contrast, in the case where a balloon is produced in such a manner that the parting line is on the major axis of the pressure-receiving portion, the parting line serves as a bend portion when the balloon is compressed, so there is an advantage in that measurements of a pressure in the oral cavity are not affected.

Hereinafter, a balloon for measuring a pressure related to the oral cavity and a method for producing the same according to embodiments of the present invention will be described with reference to the drawings.

Embodiment 1

FIG. 1 is a schematic diagram showing an apparatus for measuring a pressure related to the oral cavity according to Embodiment 1. A probe 10 including a balloon 1 is connected to a pressure-detecting unit 7 via an apparatus-side tube 6. The probe 10 has a structure in which the balloon 1 is connected to a probe tube 3 using a clamping ring 2. The balloon 1 and the probe tube 3 are fixed to each other in an airtight manner by the clamping ring 2. A hard ring 8 is mounted on the balloon 1 between a portion to be attached to the probe tube 3 and an inflated portion.

The probe tube 3 has a male fitting portion 4, and the probe tube 3 and the apparatus-side tube 6 are connected to each other by fitting the male fitting portion 4 into a female fitting portion 5 provided on the apparatus-side tube 6. A valve 11 is provided between the apparatus-side tube 6 and the pressure-detecting unit 7, and a pressurizing unit 12 is connected via the valve 11. A display unit 9 is connected to the pressure-detecting unit 7. It should be noted that the pressure-detecting unit 7, the valve 11, the pressurizing unit 12, and the display unit 9 may be integrated into a single device.

With the above-described structure, the interior of the balloon 1 communicates with the pressure-detecting unit 7 through the probe tube 3 and the apparatus-side tube 6. The pressure-detecting unit 7 includes a pressure transducer that converts the air pressure into an electrical signal and an amplifier that amplifies the electrical signal, and the output from the amplifier is supplied to the display unit 9.

The male fitting portion 4 and the female fitting portion 5 are formed of for example, luer taper fitting members, and are adapted to be removably fitted together. Therefore, the probe 10 including the probe tube 3 enables an airtight connection of the balloon 1 to the pressure-detecting unit 7 in a removable manner. Moreover, if a wrapped and sterilized unit of the probe 10 is provided separately, this unit can be made separately disposable and thus can be changed each time the tongue pressure measurement is performed. Any other fitting structures can be applied to the connection between the probe tube 3 and the apparatus-side tube 6 as long as an airtight seal can be maintained.

For an airtight connection between the balloon 1 and the probe tube 3, other than by fixing with the clamping ring 2 shown in FIG. 1, a method of welding the balloon 1 and the probe tube 3 to each other with heat or a method of bonding them to each other with an adhesive also can be used.

The hard ring 8 mounted on the balloon 1 has the following functions. The first function is to prevent the balloon 1 from being pressed down by the pressure from the lips or incisors, which effects the pressure measurement. The second function is to perform positioning during the insertion of the balloon 1 into the mouth so that the hard ring 8 is located at a position in line with the lips or teeth, thereby enabling a consistent pressure measurement.

Regarding the material for the probe tube 3, a hard material is preferable in view of the ease of retention when the balloon 1 is held in the mouth. Particularly preferable materials are rigid plastics such as polypropylene, polyethylene, and polycarbonate. As for the apparatus-side tube 6, although it is preferable that the female fitting portion 5 is formed of a rigid plastic, the other portion is preferably formed of a soft plastic, such as soft polyvinyl chloride, polybutadiene, soft polypropylene, soft polyethylene, or an ethylene-vinyl acetate copolymer, in view of operability. However, an excessively flexible and thin material makes it difficult to perform an accurate pressure measurement, so that a tube having a moderate degree of flexibility and wall thickness is preferable.

The pressure-detecting unit 7 is composed of, for example, a pressure-introducing type strain gauge pressure transducer so as to convert the air pressure into an electrical signal. The pressure-detecting unit 7 may include an amplifier for amplifying a signal before the signal is output to the display unit 9. Any other type of pressure transducer may be used as the pressure transducer.

To measure the tongue pressure, the valve 11 is opened, and the interior of the balloon 1 is pressurized by the pressurizing unit 12 to a predetermined pressure. The pressurized balloon 1 is placed in the mouth to measure the maximum tongue pressure or the tongue pressure during deglutition. The pressure in the balloon 1 is not particularly limited, but is preferably about 5 to 30 kPa. It should be noted that the valve 11 is not essential depending on the structure of the pressurizing unit 12, and a structure in which the pressurizing unit 12 is connected directly to the apparatus-side tube 6 is also applicable.

Figure 2:
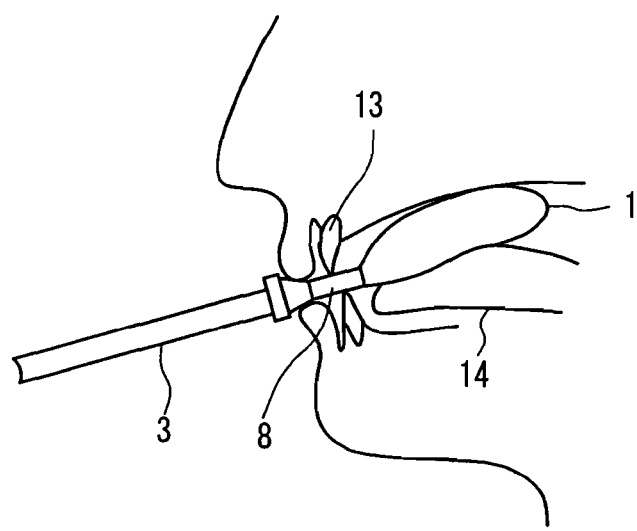
FIG. 2 is a cross-sectional view showing a state in which a probe of the apparatus shown in FIG. 1 is being used.

In measuring the tongue pressure, as shown in FIG. 2, the balloon 1 is held in the mouth with the hard ring 8 located at a position corresponding to the lips or the teeth 13. In this state, the balloon 1 is pressed by the tongue 14 at a maximum pressure; thus, the maximum tongue pressure can be measured. Moreover, the tongue pressure during deglutition can be measured by holding the balloon 1 in the mouth with a liquid kept in the mouth and continuously monitoring changes in the pressure during the deglutition movement. In such a manner, the pressures produced by various types of movement can be measured.

It should be noted that it is not essential to form a probe 10 in which the balloon 1 and the probe tube 3 are connected to each other, and it is possible to configure the balloon 1 and the pressure-detecting unit 7 to be connected directly to each other using a suitable connecting member.

Figure 3A:
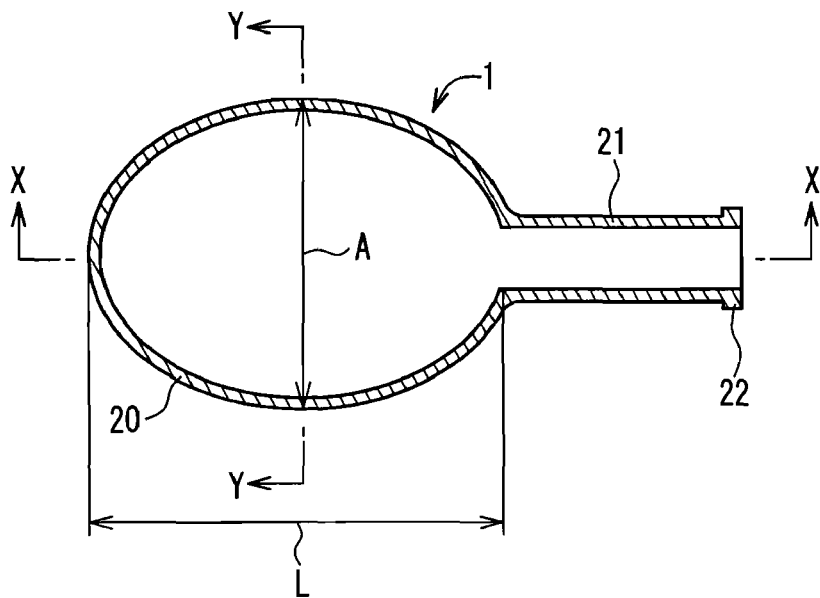
FIG. 3A is a cross-sectional view showing a planar shape of a balloon used for the apparatus shown in FIG. 1.
Figure 3B:
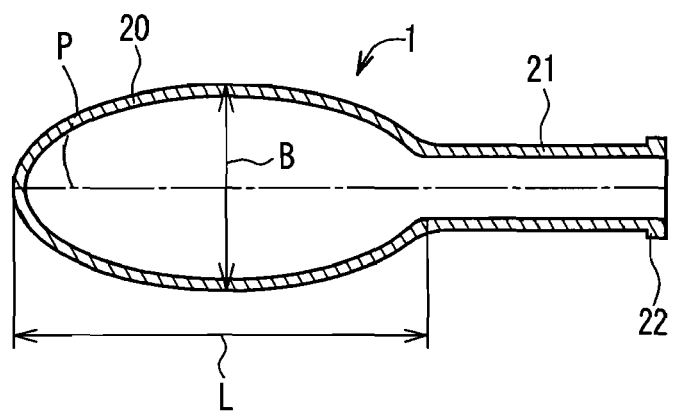
FIG. 3B is a cross-sectional view showing a side shape of the balloon, taken along line X-X in FIG. 3A.
Figure 4:
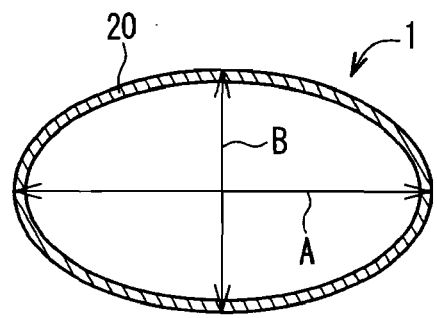
FIG. 4 is a cross-sectional view showing a transverse cross-sectional shape of the balloon, taken along line Y-Y in FIG. 3A.

Next, the balloon 1 for measuring a pressure related to the oral cavity used in the present embodiment will be described in detail. FIGS. 3 and 4 show a cross-sectional shape of the balloon 1 for measuring a pressure related to the oral cavity FIG. 3A shows a planar shape of the balloon 1 in cross section. FIG. 3B shows a side shape thereof, i.e., the shape of an X-X cross section in FIG. 3A. FIG. 4 shows a transverse cross-sectional shape of the balloon 1, i.e., the shape of a Y-Y cross section in FIG. 3A.

The balloon 1 has a pressure-receiving portion 20 that is formed so as to be swollen out into a flattened ellipsoidal shape or a flattened almond shape, a tubular portion 21 that is formed integrally with the pressure-receiving portion 20 and that communicates with the interior of the pressure-receiving portion 20, and a flange portion 22 that is formed around the periphery of an opening end of the tubular portion 21. The transverse cross-section of the balloon 1 shown in FIG. 4 is a cross section orthogonal to the axial direction of the tubular portion 21. The length of the major axis of this transverse cross-section is indicated by A, and the length of the minor axis is indicated by B. The transverse cross-section shown in FIG. 4 is a transverse cross-section at a position at which the length A of the major axis is at a maximum. A parting line P extending in a longitudinal direction in FIG. 3B is formed by blow molding as described later and passes close to both ends of the major axis of the pressure-receiving portion 20.

The transverse cross-section of the pressure-receiving portion 20 shown in FIG. 4 has a flattened outer circumferential shape with an oblateness $f=(A-B)/A$, where A represents the length of the major axis of the outer circumferential shape and B represents the length of the minor axis thereof, being set to a range of $0.1 \leq f \leq 0.7$ at the position at which the length A of the major axis is at a maximum. An oblateness f of 0.1 or more can provide a sufficient effect for practical use. An oblateness f exceeding 0.7 results in an excessively flattened balloon, which makes it difficult to take measurements. More preferably, the oblateness f is set to a range of $0.15 \leq f \leq 0.35$.

Moreover, the outer diameter of the tubular portion 21 is set so that the ratio of the outer diameter to the length B of the minor axis of the pressure-receiving portion 20 is 5 to 50%. From a study on the size that makes it possible to close the mouth firmly after insertion of the balloon into the oral cavity and, during actual measurement of tongue pressure, to keep the same state as when the mouth is closed while the examination is being performed, it was found that an outer diameter of the tubular portion 21 that satisfies the above-described relationship between the outer diameter and the length B of the minor axis of the pressure-receiving portion 20 is suitable for practical use.

The balloon 1 is formed using a thermoplastic elastomer, and the wall thickness of the pressure-receiving portion 20 can be set to a range of 0.1 to 2.0 mm. More preferably, the wall thickness is set to a range of 0.2 to 1.6 mm. The length L of the pressure-receiving portion 20 in the longitudinal direction can be set to a range of 15 to 30 mm. As for specific numerical values of the dimensions of the pressure-receiving portion 20, the length A of the major axis can be set to 15 to 25 mm, and the length B of the minor axis can be set to 10 to 20 mm.

As an example, the following numerical values of the dimensions of the balloon 1 can be actually set: the length L in the longitudinal direction=25 mm, the length A of the major axis of the pressure-receiving portion 20=18 mm, the length B of the minor axis of the pressure-receiving portion 20=12 mm, and the oblateness $(A-B)/A=0.33$. As another example, the following numerical values also can be actually set: the length L in the longitudinal direction=25 mm, the length A of the major axis of the pressure-receiving portion 20=18 mm, the length B of the minor axis of the pressure-receiving portion 20=15 mm, and the oblateness $(A-B)/A=0.17$. Moreover, the length of the tubular portion 21 including the flange portion 22 can be about 12 mm, the outer diameter of the tubular portion can be about 5.0 mm, and the wall thickness of the flange portion 22 can be about 1 mm.

For example, an olefin elastomer, a styrene elastomer, a polyester elastomer, an urethane elastomer, or the like or a material prepared by suitably combining these elastomers can be used as the thermoplastic elastomer for forming the balloon 1. A styrene elastomer or an olefin elastomer is preferably used.

According to the balloon for measuring a pressure related to the oral cavity of the present embodiment, the pressure-receiving portion has a flattened shape and, thus, an effect that makes it easy to stably compress the balloon with the tongue or the like can be obtained. Therefore, it is possible to reduce sufficiently the volume of the balloon by compressing, so as to increase the compressibility of air. For this reason, the air pressure in the balloon can be changed significantly and stably, and the precision in the case of measuring the pressure applied to the balloon based on changes in the air pressure is made stable.

Figure 5:
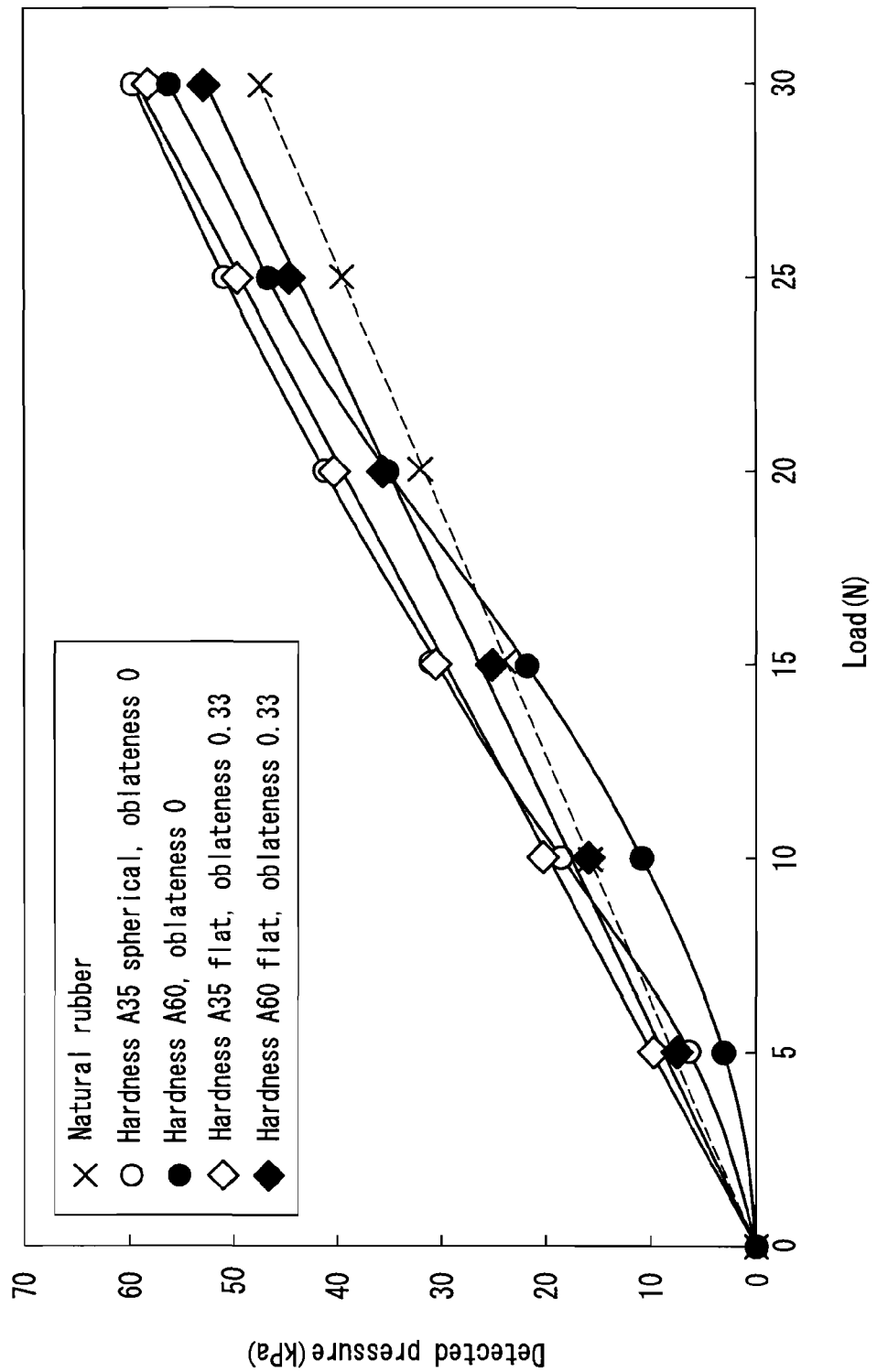
FIG. 5 is a graph showing the relationship between a load and a detected pressure in the case of balloons having a flattened transverse cross-section or a circular transverse cross-section.

Next, an effect of the use of the balloon for measuring a pressure related to the oral cavity of the present embodiment on properties indicating the relationship between the load and the detected pressure will be described with reference to FIG. 5. In the graph in FIG. 5, the horizontal axis represents the load (N) applied to the balloon, and the vertical axis represents the detected pressure (kPa) detected using the balloon. Open circle marks show the properties of a balloon that is formed using a styrene thermoplastic elastomer having a hardness of A35 and that has a pressure-receiving portion having a circular transverse cross-sectional shape, indicating the relationship between the load and the detected pressure. Solid circle marks show the properties of a balloon that is formed using a styrene thermoplastic elastomer having a hardness of A60 and that has a pressure-receiving portion having a circular transverse cross-sectional shape. For both balloons, the relationship is not represented by a straight line, but rather by a sigmoid curve. Moreover, open diamond marks show the properties of a balloon that is formed using a thermoplastic elastomer having a hardness of A35 and that has a pressure-receiving portion having a transverse cross-section with an oblateness of 0.33 in accordance with the present embodiment. Solid diamond marks show the properties of a balloon that is formed using a thermoplastic elastomer having a hardness of A60 and that has a pressure-receiving portion having a transverse cross-section with an oblateness of 0.33 in accordance with the present embodiment. Both balloons generally show favorable linearity. The properties in the case of using a natural rubber are shown by cross marks for reference.

As described above, by forming a balloon so as to have a flattened transverse cross-sectional shape in accordance with the present embodiment, even in the case where the balloon is manufactured using a thermoplastic elastomer, a favorably linear relationship between the load and the detected pressure can be obtained, and the precision of measurement can be ensured by suppressing variations in the pressure detection sensitivity depending on the range of the load applied to the balloon. Moreover, a reduction in the sensitivity in a low-load region due to sigmoidal properties, such as the properties of the balloon (solid circle marks) that is formed using the thermoplastic elastomer having a hardness of A60 and that has the pressure-receiving portion having a circular transverse cross-sectional shape, does not occur. Thus, even in a low-load region, the pressure can be detected with the same sensitivity and precision as in a high-load region.

Figure 6:
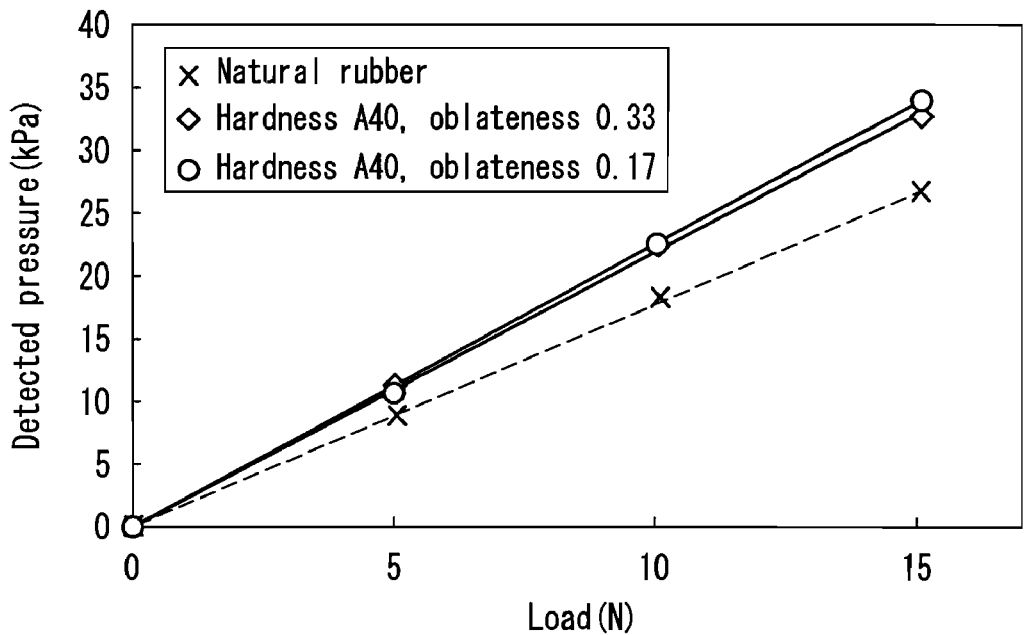
FIG. 6 is a graph showing the relationship between the load and the detected pressure in the case of balloons having transverse cross-sections with different degrees of oblateness.

Next, FIG. 6 shows the properties indicating the relationship between the load and the detected pressure in the case of balloons for measuring a pressure related to the oral cavity having transverse cross-sections with various different degrees of oblateness. In the graph in FIG. 6, the horizontal axis represents the load (N) applied to the balloon, and the vertical axis represents the detected pressure (kPa) detected using the balloon. A thermoplastic elastomer having a hardness of A40 was used. Open diamond marks show the properties of a balloon that has a pressure-receiving portion having a transverse cross-section with an oblateness of 0.33, and open circle marks show the properties of a balloon with an oblateness of 0.17. The properties in the case of using a natural rubber are shown by cross marks for reference.

Figure 7:
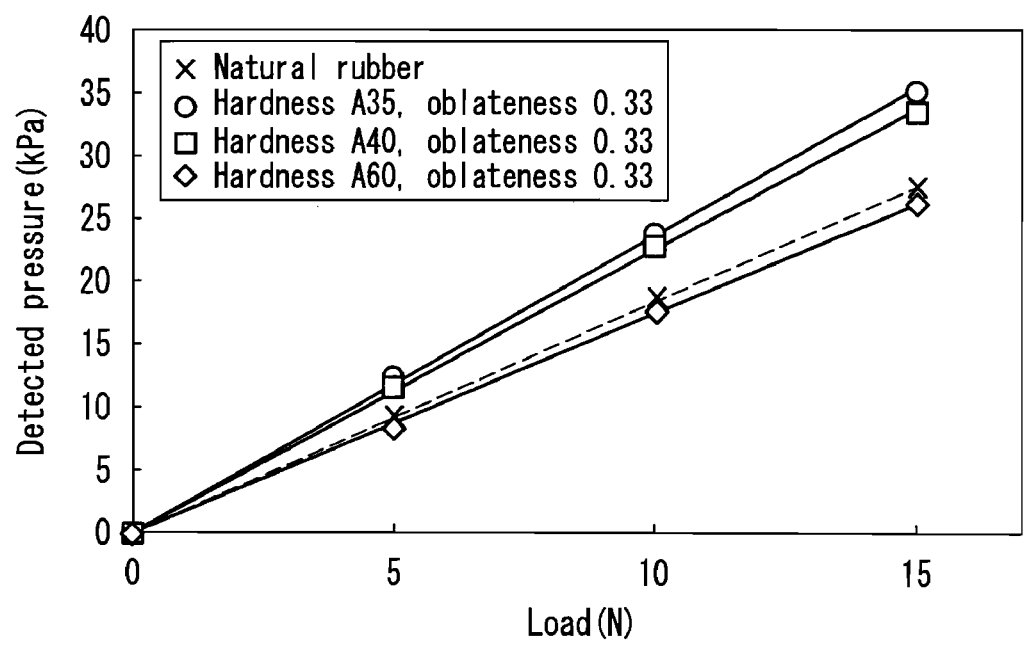
FIG. 7 is a graph showing the relationship between the load and the detected pressure in the case of balloons that are formed using thermoplastic elastomers with different degrees of hardness.

Next, FIG. 7 shows the results of research on a suitable range of the hardness of the thermoplastic elastomer used to form the balloon for measuring a pressure related to the oral cavity. In the graph in FIG. 7, the horizontal axis represents the load (N) applied to a balloon, and the vertical axis represents the detected pressure (kPa) detected using the balloon. The oblateness of the transverse cross-section of the pressure-receiving portion was set to 0.33. Open circle marks show the properties of a balloon that is formed using a thermoplastic elastomer having a hardness of A35, open square marks show the properties of a balloon that is formed using a thermoplastic elastomer having a hardness of A40, and open diamond marks show the properties of a balloon that is formed using a thermoplastic elastomer having a hardness of A60. The properties in the case of using a natural rubber are shown by cross marks for reference.

It is found from FIGS. 6 and 7 that as long as the hardness of the thermoplastic elastomer is within a range of A35 to 60, sufficiently favorable properties for practical use can be obtained in the oblateness (range of 0.15 to 0.35. It should be noted that the measurement sensitivity is slightly lower in the case where the thermoplastic elastomer having a hardness of A60 is used, but there is no problem in actually using the balloon.

Moreover, by setting the wall thickness of the pressure-receiving portion 20 to a moderate thickness of 0.1 to 2.0 mm, the occurrence of a local bulge can be prevented while improving the measurement precision of the detected pressure.

Embodiment 2

Figure 8:
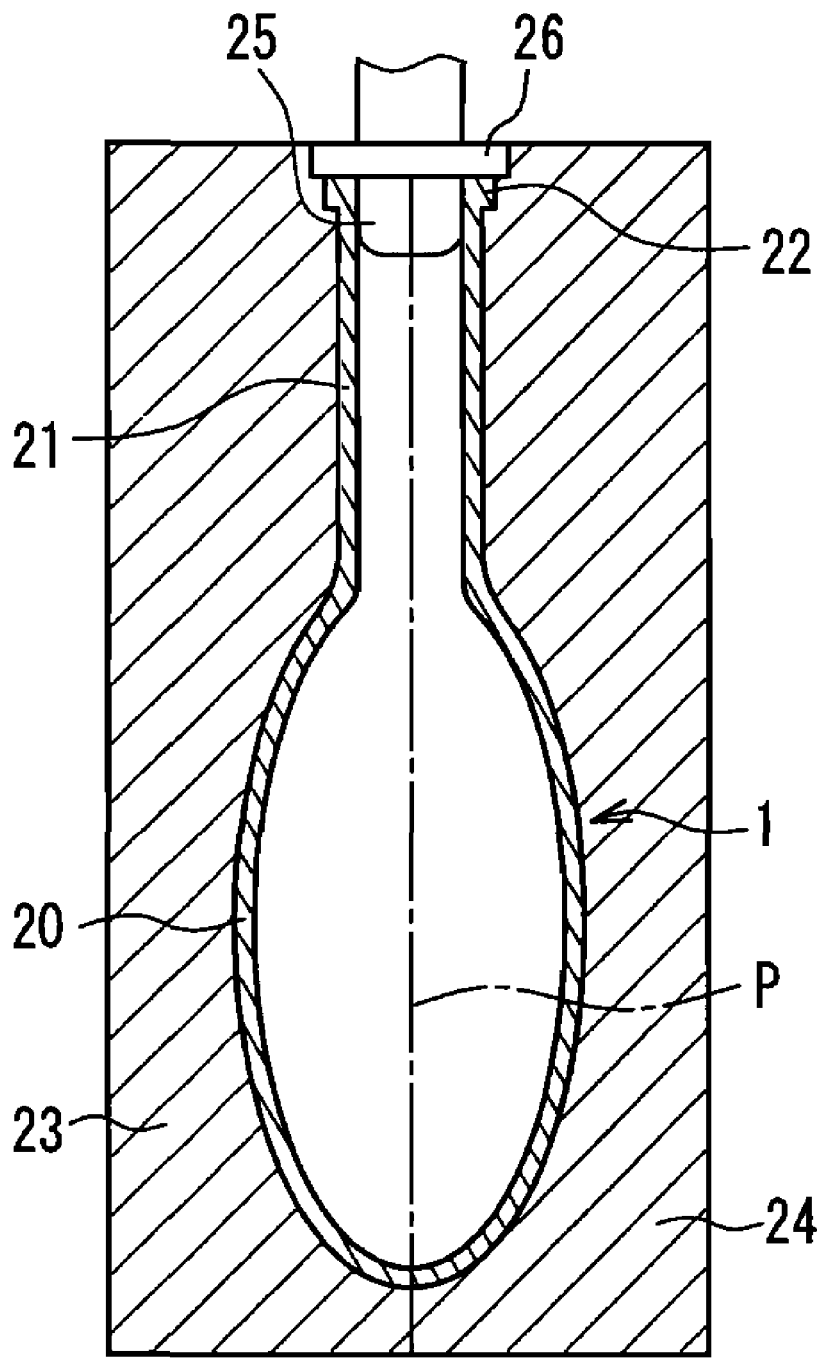
FIG. 8 is a cross-sectional view showing a metal mold that is used in a method for producing the balloon for measuring a pressure related to the oral cavity shown in FIGS. 3 and 4 by using blow molding.

A method for producing a balloon for measuring a pressure related to the oral cavity according to Embodiment 2 of the present invention will be described with reference to FIG. 8. FIG. 8 is a cross-sectional view showing a metal mold that is used when the balloon 1 described in Embodiment 1 is formed by blow molding. In the following description, the components of the balloon 1 are given the same reference numerals as used in, for example, FIG. 3A.

This metal mold is configured from split mold sections 23 and 24 that regulate the outer shape of the balloon 1. In a blow molding process, a parison of a thermoplastic elastomer is extruded into the split mold sections 23 and 24, and then the split mold sections 23 and 24 are closed. A blowing nozzle 25 is inserted from one end side (an upper end side in the drawing) of the parting line P of the closed split mold sections 23 and 24 so that a tip of the nozzle is inserted into the parison. At the same time, an open region on the upper end side of the split mold sections 23 and 24 is blocked with a blocking portion 26 of the blowing nozzle 25, and air is blown through the blowing nozzle 25 to inflate the parison, thereby shaping the balloon 1.

In the process of forming the balloon 1 by blow molding, the outer shape of the balloon 1 is regulated by inner faces of the split mold sections 23 and 24. Thus, after shaping, when the split mold sections 23 and 24 are opened at the parting line P, the balloon 1 can be removed easily from the metal mold. Therefore, it is possible to make the pressure-receiving portion 20 sufficiently larger than the tubular portion 21. Moreover, blow molding can increase the precision of the thickness of the pressure-receiving portion 20.

The parting line P of the split mold sections 23 and 24 is positioned so as to be in a plane containing the axis of the tubular portion 21 and the major axis of the pressure-receiving portion 20. If the parting line P is not on the major axis of the pressure-receiving portion 20, in some cases, the inflated balloon 1 may be distorted, and when a distorted portion is compressed, the following problems arise: variations in the measurement results are likely to occur, it is unpleasant to touch, and so on. In contrast, in the case where the parting line P is positioned on the major axis of the pressure-receiving portion 20 during production, the parting line P serves as a bend portion when the balloon 1 is compressed, so as to obtain an advantage that the results of the measurement of a pressure in the oral cavity are stable.

Moreover, as mentioned in the description of Embodiment 1, it is desirable that the outer diameter of the tubular portion 21 is set so that the ratio of the outer diameter to the length B of the minor axis of the pressure-receiving portion 20 is 5 to 50%. However, under the present circumstances, a balloon having such a ratio can be produced only by blow molding.

It should be noted that although examples of the flattened shape of the balloon according to the present invention include an elliptical shape or an almond shape as described above, a modified shape other than these shapes also can be used as long as the oblateness is set to the predetermined range.

INDUSTRIAL APPLICABILITY

The balloon for measuring a pressure related to the oral cavity according to the present invention is capable of changing the air pressure significantly and stably and increasing the precision of the measurement of a pressure related to the oral cavity and, therefore, is useful for an apparatus for measuring the tongue pressure, the pressure of the muscles under the tongue, the lip pressure, the cheek pressure, and the like.

The invention claimed is:

1. A balloon for measuring a pressure related to an oral cavity, comprising:
a pressure-receiving portion that is formed of an elastic material and that internally forms a closed space, the pressure-receiving portion being configured to be placed in the oral cavity; and
a tubular portion that is formed integrally with the pressure-receiving portion,
the balloon being configured to detect an air pressure in an interior of the pressure-receiving portion by communicating the interior of the pressure-receiving portion with a pressure detector through an opening end of the tubular portion,
wherein the pressure-receiving portion and the tubular portion are formed of a thermoplastic elastomer, and
a transverse cross-section of the pressure-receiving portion orthogonal to an axial direction of the tubular portion has a flat outer circumferential shape with an oblateness $f=(A-B)/A$, where A represents a length of a major axis of the outer circumferential shape and B represents a length of a minor axis thereof, being set to a range of $0.1 \leq f \leq 0.7$ at a position at which the length A of the major axis is at a maximum.

2. The balloon for measuring a pressure related to an oral cavity according to claim 1, wherein a ratio of an outer diameter of the tubular portion to the length B of the minor axis of the pressure-receiving portion is 5 to 50%.

3. The balloon for measuring a pressure related to an oral cavity according to claim 1, wherein the hardness of the thermoplastic elastomer based on the type A durometer hardness test specified in JIS K 6253 is within a range of A20 to A60.

4. The balloon for measuring a pressure related to an oral cavity according to claim 1, wherein the pressure-receiving portion has a wall thickness of 0.1 to 2.0 mm.

5. The balloon for measuring a pressure related to an oral cavity according to claim 1, wherein the pressure-receiving portion has a length of 15 to 30 mm, and a transverse cross-section of the pressure-receiving portion having maximum dimensions has an outer circumferential shape in which the length A of the major axis is 15 to 25 mm and the length B of the minor axis is 10 to 20 mm.

6. A probe for measuring a pressure related to an oral cavity, comprising:
the balloon for measuring a pressure related to an oral cavity according to claim 1; and
a cylindrical probe tube that is coupled at one end to the tubular portion of the balloon in an airtight manner,
wherein a coupling portion that can be removably coupled to the pressure detector is formed at the other end of the probe tube.

7. An apparatus for measuring a pressure related to an oral cavity, comprising:
the balloon for measuring a pressure related to an oral cavity according to claim 1;
a pressure detector; and
a connecting member that provides a connection between the pressure detector and the balloon for measuring a pressure related to an oral cavity to allow the interior of the balloon to communicate with the pressure detector,
wherein the air pressure in the interior of the balloon can be detected by the pressure detector.

* * * * *